(12) United States Patent
Reddy et al.

(10) Patent No.: US 9,676,690 B2
(45) Date of Patent: Jun. 13, 2017

(54) PROCESSES FOR MAKING MAGNOLOL DERIVATIVES

(71) Applicant: Colgate-Palmolive Company, New York, NY (US)

(72) Inventors: Basi V. Subba Reddy, Hyderabad (IN); Ravi Subramanyam, Mumbai (IN); Shashank Potnis, Thane (IN); Jhillu Singh Yadav, Hyderabad (IN)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/762,998

(22) PCT Filed: Jan. 23, 2013

(86) PCT No.: PCT/IN2013/000049
§ 371 (c)(1),
(2) Date: Jul. 23, 2015

(87) PCT Pub. No.: WO2014/115156
PCT Pub. Date: Jul. 31, 2014

(65) Prior Publication Data
US 2015/0361017 A1    Dec. 17, 2015

(51) Int. Cl.
| | | |
|---|---|---|
| *C07C 41/30* | (2006.01) |
| *C07C 41/36* | (2006.01) |
| *C07C 37/055* | (2006.01) |
| *A61Q 11/00* | (2006.01) |
| *C07C 37/00* | (2006.01) |
| *C07C 41/16* | (2006.01) |
| *A61K 8/33* | (2006.01) |
| *C07C 41/06* | (2006.01) |

(52) U.S. Cl.
CPC .............. *C07C 37/055* (2013.01); *A61K 8/33* (2013.01); *A61Q 11/00* (2013.01); *C07C 37/003* (2013.01); *C07C 41/06* (2013.01); *C07C 41/16* (2013.01)

(58) Field of Classification Search
None
See application file for complete search history.

(56) References Cited

U.S. PATENT DOCUMENTS

| | | |
|---|---|---|
| 6,500,409 B1 | 12/2002 | Scherl et al. |
| 8,519,197 B2 | 8/2013 | Reddy et al. |
| 8,956,592 B2 | 2/2015 | Yang et al. |
| 9,000,231 B2 | 4/2015 | Naik et al. |
| 9,045,397 B2 | 6/2015 | Naik et al. |
| 2012/0294812 A1 | 11/2012 | Fei et al. |

OTHER PUBLICATIONS

Alexakis et al., 2004, "Biphenol-Based Phosphoramidite Ligands for the Enantioselective Copper-Catalyzed Conjugate Addition of Diethylzinc," The Journal of Organic Chemistry 69(17):5660-5667.
Chattopadhyay et al., 2006, "Sequential Double Claisen Rearrangement and Two-Directional Ring-Closing Metathesis as a Route to Various Benzofused Bisoxepin and Bisoxocin Derivatives," Synlett 2006(14):2211-2214.
International Search Report and Written Opinion in International Application No. PCT/IN2013/000049, mailed Sep. 23, 2013.
Kong et al., 2004, "Cytotoxic neolignans: an SAR study," Bioorganic & Medicinal Chemistry Letters 15:163-166.
Reinhoudt et al., 1981, "Crown ethers with converging neutral binding sites," Tetrahedron 37(9):1753-1762.
Sorell et al., 1985, "3,3'-Disubstituted 2,2'-biphenols. Synthesis of nonplanar, tetradentate chelating ligands," The J. of Organic Chemistry 50(26):5765-5769.
Written Opinion in International Application No. PCT/IN2013/000049 mailed Dec. 22, 2014.

*Primary Examiner* — Rosalynd Keys

(57) ABSTRACT

Described herein are high yield methods for making magnolol derivatives, together with novel intermediates and uses thereof.

7 Claims, No Drawings

PROCESSES FOR MAKING MAGNOLOL DERIVATIVES

BACKGROUND

There is a need for safe, effective antibacterial and anti-inflammatory agents for use in oral care compositions. Magnolia extract is known to contain compounds having antibacterial and/or anti-inflammatory properties, and such compounds have been the focus of considerable interest for use in oral care compositions. The use of such compounds in oral care compositions is described, for example, in WO2001/085116, WO 2011/106492 and WO 2011/106493, the contents of which application are incorporated herein by reference. Methods of synthesizing magnolol are disclosed, e,g, in WO 2011/106003. Synthetic non-natural analogs of various components of magnolia extract are also known to have antibacterial activity, but the compounds are in some cases expensive to synthesize.

Isomagnolol (3,3'-diallyl-biphenyl-2,2'-diol) and tetra-hydro-isomagnolol, (3,3'-dipropyl-biphenyl-2,2'-diol), are broad spectrum antibacterial and anti-inflammatory agents with potential applications in oral care and personal care products. Existing synthetic methods involve costly reagents and poor yields. There is a need for simple, high yield synthetic procedures to make such compounds.

SUMMARY

The invention provides a simple, efficient, two or three-step synthesis for isomagnolol derivatives, comprising O-alkylating biphenyl-2,2'-diol with an allyl halide, heating at reflux to obtain 3,3'-diallyl-biphenyl-2,2'-diol, and optionally reducing the allyl moieties to obtain (3,3'-dipropyl-biphenyl-2,2'-diol).

In another embodiment, the invention provides a novel and useful intermediate, 2,2'-di(allyloxy)-biphenyl.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The invention thus provides a method (Method 1) for making isomagnolol (3,3'-diallyl-biphenyl-2,2'-diol) or tetrahydro-isomagnolol, (3,3'-dipropyl-biphenyl-2,2'-diol), comprising heating 2,2'-di(allyloxy)-biphenyl until it is substantially converted to 3,3'-diallyl-biphenyl-2,2'-diol, 1.1. Method 1 wherein the 2,2'-di(allyloxy)-biphenyl is heated neat at a temperature in excess of 175° C., e.g. 200-220° C., e.g., about 210° C.
1.2. Any of the foregoing methods wherein the period of heating is at least 4 hrs, e.g. 408 hrs, e.g. about 6 hrs.
1.3. Any of the foregoing methods further comprising hydrogenating the 3,3'-diallyl-biphenyl-2,2'-diol e.g., in the presence of a metal catalyst, e.g., a palladium or nickel catalyst, to obtain 3,3'-dipropyl-biphenyl-2,2'-diol.
1.4. Any of the foregoing methods further comprising reacting biphenyl-2,2'-diol with an allyl halide, e.g., 3-chloroprop-1-ene or 3-bromoprop-1-ene to obtain 2,2'-di(allyloxy)-biphenyl.

In another embodiment, the invention provides 2,2'-di(allyloxy)-biphenyl, together with methods of making it comprising reacting biphenyl-2,2'-diol with an allyl halide, e.g., 3-chloroprop-1-ene or 3-bromoprop-1-ene, e.g., in the presence of a base, e.g. potassium carbonate, in the presence of a polar aprotic solvent, e.g., acetone, e.g., at reflux.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The invention is further described in the following examples. The examples are merely illustrative and do not in any way limit the scope of the invention as described and claimed.

EXAMPLES

Example 1

Synthesis of 2,2'-di(allyloxy)-biphenyl

In the first step of the synthesis, 2,2'-di(allyloxy)-biphenyl is made as follows, using either allyl bromide or allyl chloride to react with biphenyl-2,2'-diol:

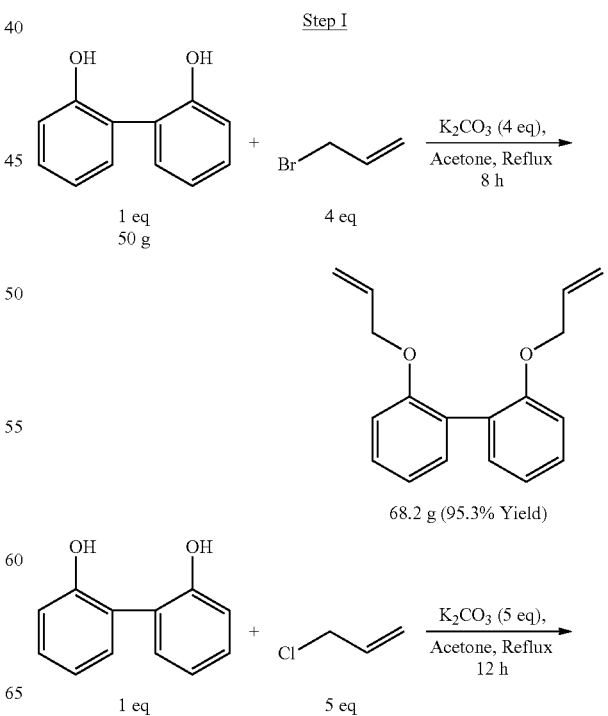

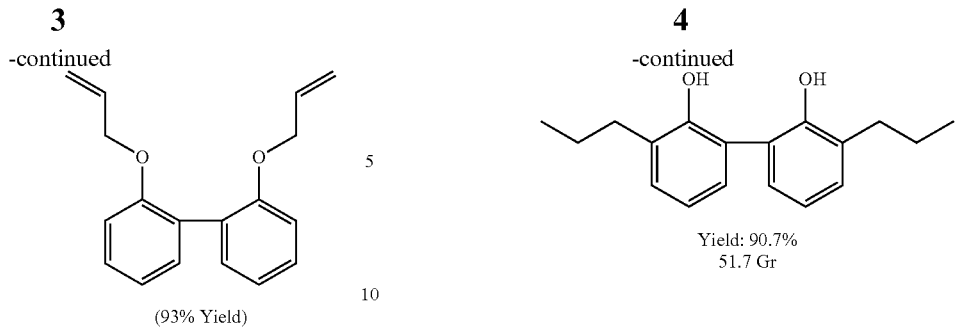

(93% Yield)

Example 2

Synthesis of 3,3'-diallyl-biphenyl-2,2'-diol (isomagnolol)

3,3'-diallyl-biphenyl-2,2'-diol is made as follows, simply by heating the material of the previous example:

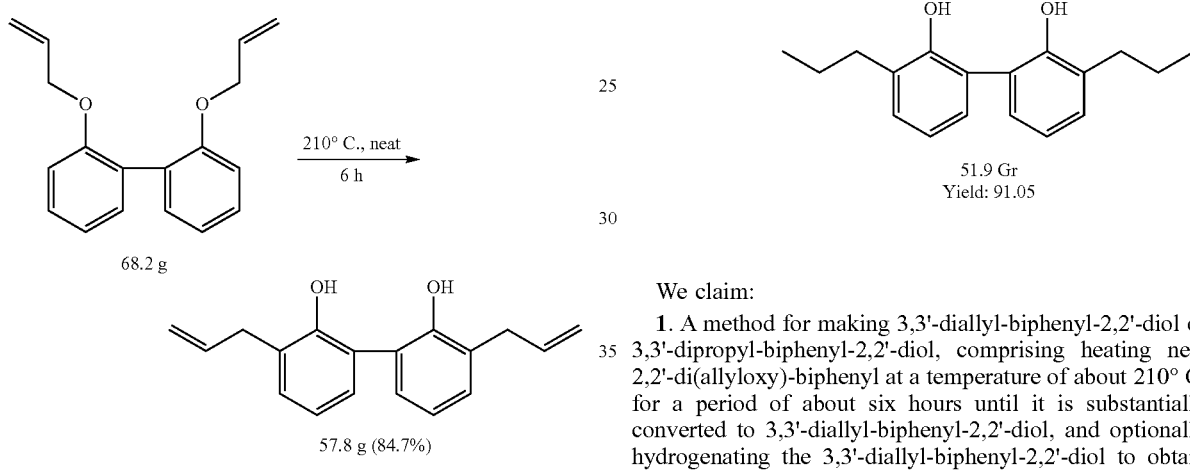

Example 3

Synthesis of 3,3'-dipropyl-biphenyl-2,2'-diol (tetrahydro-isomagnolol)

3,3'-diallyl-biphenyl-2,2'-diol is hydrogenated in the presence of a metal catalyst to obtain the title compound:

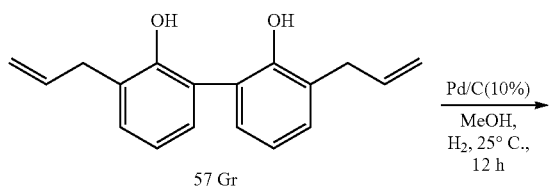

We claim:

1. A method for making 3,3'-diallyl-biphenyl-2,2'-diol or 3,3'-dipropyl-biphenyl-2,2'-diol, comprising heating neat 2,2'-di(allyloxy)-biphenyl at a temperature of about 210° C. for a period of about six hours until it is substantially converted to 3,3'-diallyl-biphenyl-2,2'-diol, and optionally hydrogenating the 3,3'-diallyl-biphenyl-2,2'-diol to obtain 3,3'-dipropyl-biphenyl-2,2'-diol.

2. The method of claim 1, further comprising reacting biphenyl-2,2'-diol with an allyl halide to obtain 2,2'-di(allyloxy)-biphenyl.

3. The method of claim 2 wherein the allyl halide is selected from 3-chloroprop-1-ene and 3-bromoprop-1-ene.

4. The method of claim 1 comprising hydrogenating 3,3'-diallyl-biphenyl-2,2'-diol to obtain 3,3'-dipropyl-biphenyl-2,2'-diol.

5. The method of claim 4 wherein the hydrogenation is accomplished using a metal catalyst.

6. The method of claim 4, wherein the hydrogenation is accomplished with palladium/10% charcoal in methanol under hydrogen at 25° C. for 12 hours.

7. The method of claim 5, wherein the metal catalyst is Raney nickel.

* * * * *